United States Patent [19]
Leagre

[11] Patent Number: 6,129,082
[45] Date of Patent: *Oct. 10, 2000

[54] SLEEVED FILTER FOR A BREATHING CIRCUIT

[75] Inventor: Michael A. Leagre, Fishers, Ind.

[73] Assignee: King Systems Corporation, Noblesville, Ind.

[*] Notice: This patent is subject to a terminal disclaimer.

[21] Appl. No.: 09/294,425

[22] Filed: Apr. 19, 1999

Related U.S. Application Data

[63] Continuation of application No. 08/925,116, Sep. 8, 1997, Pat. No. 5,901,705.

[51] Int. Cl.[7] .............................. A62B 7/10; A62B 23/02
[52] U.S. Cl. .............................. 128/205.29; 128/205.27; 128/909
[58] Field of Search ................ 128/201.25, 202.27, 128/203.27, 205.29, 909, 911, 912, DIG. 26

[56] References Cited

U.S. PATENT DOCUMENTS

| | | |
|---|---|---|
| 3,566,867 | 3/1971 | Dryden . |
| 4,133,656 | 1/1979 | Kippel et al. .............................. 55/274 |
| 4,265,235 | 5/1981 | Fukunaga . |
| 5,083,561 | 1/1992 | Russo ................................. 128/207.16 |
| 5,088,486 | 2/1992 | Jinotti ................................ 128/207.14 |
| 5,139,018 | 8/1992 | Brodsky et al. .................... 128/207.14 |
| 5,220,916 | 6/1993 | Russo ................................. 128/207.16 |
| 5,269,756 | 12/1993 | Dryden ....................................... 604/54 |
| 5,333,606 | 8/1994 | Schneider et al. ................. 128/200.24 |
| 5,343,857 | 9/1994 | Schneider et al. ................. 128/202.27 |
| 5,355,876 | 10/1994 | Brodsky et al. .................... 128/202.27 |
| 5,377,670 | 1/1995 | Smith . |
| 5,404,873 | 4/1995 | Leagre et al. . |
| 5,433,221 | 7/1995 | Adair ....................................... 128/849 |
| 5,645,048 | 7/1997 | Brodsky et al. .................... 128/202.27 |
| 5,715,815 | 2/1998 | Lorenzen et al. . |
| 5,735,266 | 4/1998 | Smith . |
| 5,901,705 | 5/1999 | Leagre ................................ 128/207.14 |

*Primary Examiner*—John G. Weiss
*Assistant Examiner*—Joseph F. Weiss, Jr.
*Attorney, Agent, or Firm*—E. Victor Indiano; Bose McKinney & Evans LLP

[57] ABSTRACT

A sleeved filter apparatus prevents germs from becoming resident on both the interior and exterior of a breathing device. The sleeved filter apparatus includes a filter member and a sleeve member. The filter member is composed of a first and second enclosure half which are sealed on their interior ends. The external ends of the two enclosure halves have connectors for connecting the sleeved filter apparatus to a breathing device and/or a patient airway component. A filter element is disposed inside the filter member enclosure for preventing gases from flowing between the first connector and the second connector of the filter member without passing through the filter element. This filter member prevents germs from passing between the patient and the interior of the breathing device. The sleeve member is made of a flexible material, and has a first open end, a second open end, and a middle portion extending between the first open end and the second open end. The first open end of the sleeve member is sealingly engaged to the filter member. The sleeve member has a diameter sized to surround the breathing circuit, and a length sufficient to extend along most or all of the entire length of the breathing circuit. The sleeve member prevents germs and bacteria from passing between the patient and the exterior of the breathing device. The sleeved filter apparatus is removable between procedures to permit reuse of the breathing circuit without substantial cross-contamination between patients.

12 Claims, 4 Drawing Sheets

SLEEVED FILTER FOR A BREATHING CIRCUIT

This is a continuation of application Ser. No. 08/925,116 filed Sep. 8, 1997 now U.S. Pat. No. 5,901,705.

TECHNICAL FIELD OF INVENTION

The present invention relates to breathing circuits of the type used in anesthesia and respiratory-type devices and more particularly, to a tubular sleeve and filter combination for such a breathing circuit.

BACKGROUND OF THE INVENTION

Breathing circuits have been used in the anesthesia field for many years to provide a vehicle for transferring anesthesia gas from an anesthesia machine to a patient, and to transfer exhaled gas from the patient to the anesthesia machine. Currently, two primary types of breathing circuits are used. The first type is known as a dual-limb circuit. Such a device includes an expiratory tube and an inspiratory tube that are usually connected to a 'Y' connector. The 'Y' connector is then coupled, at its patient end, to an anesthesia face mask or an endotracheal tube. The machine end of the inspiratory tube is coupled to the inspiratory port of either an anesthesia machine, or to a carbon dioxide absorber that is attached to an anesthesia machine. The machine end of the expiratory tube is attached to either the anesthesia machine, or to a carbon dioxide absorber attached to an anesthesia machine. An example of a carbon dioxide absorber is shown in Komesaroff U.S. Pat. No. 5,666,669, that issued on Oct. 22, 1996.

The other type of circuit is a "unilimb" circuit. An example of a unilimb circuit is shown in Leagre and Burrow U.S. Pat. No. 5,404,873 and Fukunaga U.S. Pat. No. 4,265,235. A unilimb breathing circuit includes an expiratory tube and an inspiratory tube that are coupled in a coaxial relation. Usually, the inspiratory tube is disposed within the interior of the expiratory tube. A patient end connector is provided for coupling the patient end of the unilimb breathing circuit to either an anesthesia face mask or an endotracheal tube. The machine end of the unilimb circuit contains a coupler having an inspiratory coupler and a separate, expiratory coupler. The inspiratory coupler is coupled to the inspiratory port of a carbon dioxide absorber or anesthesia machine, and the expiratory coupler is coupled to the expiratory port of the anesthesia machine or carbon dioxide absorber. The inspiratory coupler handles gas from the inspiratory tube, and the expiratory coupler end handles gas from the expiratory coupler.

Both the inspiratory and expiratory tubes function in a similar manner. Anesthesia gas and oxygen are directed into the inspiratory tube, where the gases travel from the machine end of the inspiratory tube to the patient end. The gases are then inhaled by the patient. When the patient exhales, his expiratory gases flow into the expiratory tube, which conveys the gases back to the carbon dioxide absorber. Within the carbon dioxide absorber, carbon dioxide is "scrubbed" from the gases to remove it from the gas stream. The expiratory gas may be then routed back into the inspiratory tube for rebreathing by the patient. Of course, it is often advisable to add oxygen and/or anesthesia gas to the rebreathed expiratory gas, to increase the oxygen and/or anesthesia content of the recycled gas being inhaled by the patient.

Devices which cover the exterior of a breathing circuit are known. For example, Smith U.S. Pat. No. 5,377,670 discloses a casing which surrounds a breathing circuit tube to define an insulating dead air space between the breathing tube and the casing for purposes of temperature retention.

One difficulty encountered with all breathing circuits is that viruses, bacteria and other germs become resident on the breathing circuit during use by a patient. To avoid cross-infection, the breathing circuit should not be used by a second patient without sterilization between uses. To help eliminate this risk of cross infection, the breathing circuit can be designed to be a "single use" breathing circuit that is discarded after a single use. An alternate way to avoid cross infection is to sterilize and autoclave the "re-usable" breathing circuit after each use.

Both of these methods have drawbacks. Autoclaving a breathing circuit after each use can result in substantial labor and processing costs. Although discarding the breathing circuit after a single use is very effective in preventing cross infection, single use circuits can result in additional costs to the hospital.

Another method for dealing with cross infection is to place a filter on the breathing circuit for filtering out bacteria and viruses, thus preventing them from becoming resident within the breathing circuit. Such filters typically act to prohibit such bacteria and viruses from becoming resident on the interior of the breathing circuit. The filter itself, upon which the bacteria and virus have become resident, can then be discarded after single patient use. Through this procedure, the breathing circuit can be reused, although the filter must be either disposed of or re-sterilized.

Although such breathing filters have proven effective in preventing bacteria and viruses from becoming resident on the interior of the inspiratory and expiratory tubes of the breathing circuits, typical filters do nothing to prevent bacteria and viruses from becoming resident on the exterior of the breathing circuit.

Pre-operatively or peri-operatively, blood and other bodily fluids often become discharged or transferred (via the practitioner's hands) from the patient being operated on, to the medical equipment and personnel within the surgical theater. These bodily fluids contain a wide variety of bacteria and viruses that are not visible to the naked eye. If the bodily fluids, and hence the viruses and bacteria, make contact with the exterior of the breathing circuit, they will become resident on the breathing circuit, and thus have the potential to cross-infect another person.

As a goal of modem surgical practice is to provide a substantially "germ free" environment, the presence of such bacteria and viruses on the exterior of the breathing circuit is undesirable, and hampers the ability of the circuit to be reused without sterilization. By preventing bacteria and viruses from becoming resident both on the interior and exterior of the breathing circuit tubes, one would enable a breathing circuit to have the potential to be reused for multiple patients, without incurring a substantial risk of cross infection among patients.

It is therefore an object of the present invention to provide an apparatus for helping to prevent bacteria and viruses from becoming resident on both the interior surfaces and exterior surfaces of an anesthesia breathing circuit.

SUMMARY OF THE INVENTION

In accordance with the present invention, a sleeved filter apparatus is provided for preventing germs from becoming resident on both the interior and exterior of a breathing device. The sleeved filter apparatus comprises a filter member having a hollow interior, a first connector and a second connector. A sleeve member has a first open end, a second open end and a middle portion extending between the first open end and the second open end. The first open end of the sleeve member is sealingly engaged to the filter member.

Preferably, the filter member is designed to be connected to a breathing device, which may comprise a tubular breathing circuit having a patient end connector and a machine end connector. The first connector of the filter member is preferably sized and shaped for being coupled to either the patient end connector and/or the machine end connector of the breathing circuit.

The sleeve member is preferably comprised of a flexible material, and has a diameter that is sized to loosely surround, and contain the tube or tubes of the breathing circuit. Although a sleeve for use with a unilimb circuit should have a generally constant diameter throughout its length, a sleeve designed for use with dual limb breathing circuits should have an expanding diameter throughout its length.

The filter member is connected to the breathing device, which may be a breathing circuit, using one of the filter member connectors. The other filter member connector could be attached to an anesthesia face mask, or an endotracheal tube. Preferably, the tubular sleeve extends along substantially the entire length of the breathing circuit, or at least so much of the length as is likely to come into contact with bodily fluids. The first end of the tubular sleeve is preferably bonded to form a seal with the filter, and is fabricated to be permanently connected to the filter member.

To attach the filter/sleeve device to an anesthesia breathing circuit, the breathing circuit port of the filter member is coupled onto the patient end connector of the anesthesia breathing circuit. The tubular sleeve is then pulled over the length of the breathing circuit. After an operation or procedure with a particular patient, the filter can then be removed, by disconnecting it from the patient end of the anesthesia breathing circuit. As the tubular sleeve is connected to the filter, pulling the filter out of engagement with the breathing circuit, and away from the breathing circuit, also pulls the tubular sleeve off the breathing circuit. The filter and tubular sleeve can then be discarded, and a new sleeved filter inserted onto the anesthesia breathing circuit for use with the next patient.

One feature of the present invention is that the filter helps to prevent bacteria and viruses from becoming resident on the interior of the breathing circuit, and the tubular sleeve helps to prevent bacteria and viruses from becoming resident on the exterior of the breathing circuit. By removing the filter and tubular sleeve from the breathing circuit after a procedure, the bacteria and viruses, which become resident primarily within the filter and on the exterior surface of the tubular sleeve, can then be discarded by discarding the tubular sleeve and filter. This leaves the breathing circuit in a sufficiently bacteria-free and virus-free condition to permit reuse of the breathing circuit by another patient.

Another feature of the present invention is that the sleeved filter apparatus of the present invention can be made relatively inexpensively, when compared to the costs of other components which typically comprise a full breathing set. Full breathing sets consist of several components, many of which are not economically feasible to either discard or sterilize after each use. The sleeved filter device will filter bacteria and viruses that are carried in the patient's breath, thus preventing the bacteria and viruses from becoming resident on the interior of the breathing device components. The sleeve, which can be sized to accommodate various types of breathing device designs, will intercept bodily fluids and other contaminants that would otherwise contact the exterior of the breathing device components. As the sleeved filter can be made relatively inexpensively it can be disposed of after each use cost effectively, while permitting the relatively more expensive components of the breathing device to be re-used, and while still protecting patients from cross-contamination.

Another feature of the present invention is that it will help reduce the clutter caused by breathing devices. Many breathing devices have several limbs running between the patient and the breathing device. The sleeve member of the present invention will surround all of these limbs and effectively create one limb running between the patient and the breathing device, thus reducing clutter and space requirements.

These and other features of the present invention will become apparent to those skilled in the art upon a review of the detailed description presented below in conjunction with the drawings.

DETAILED DESCRIPTION OF PREFERRED EMBODIMENT

Figure 1:
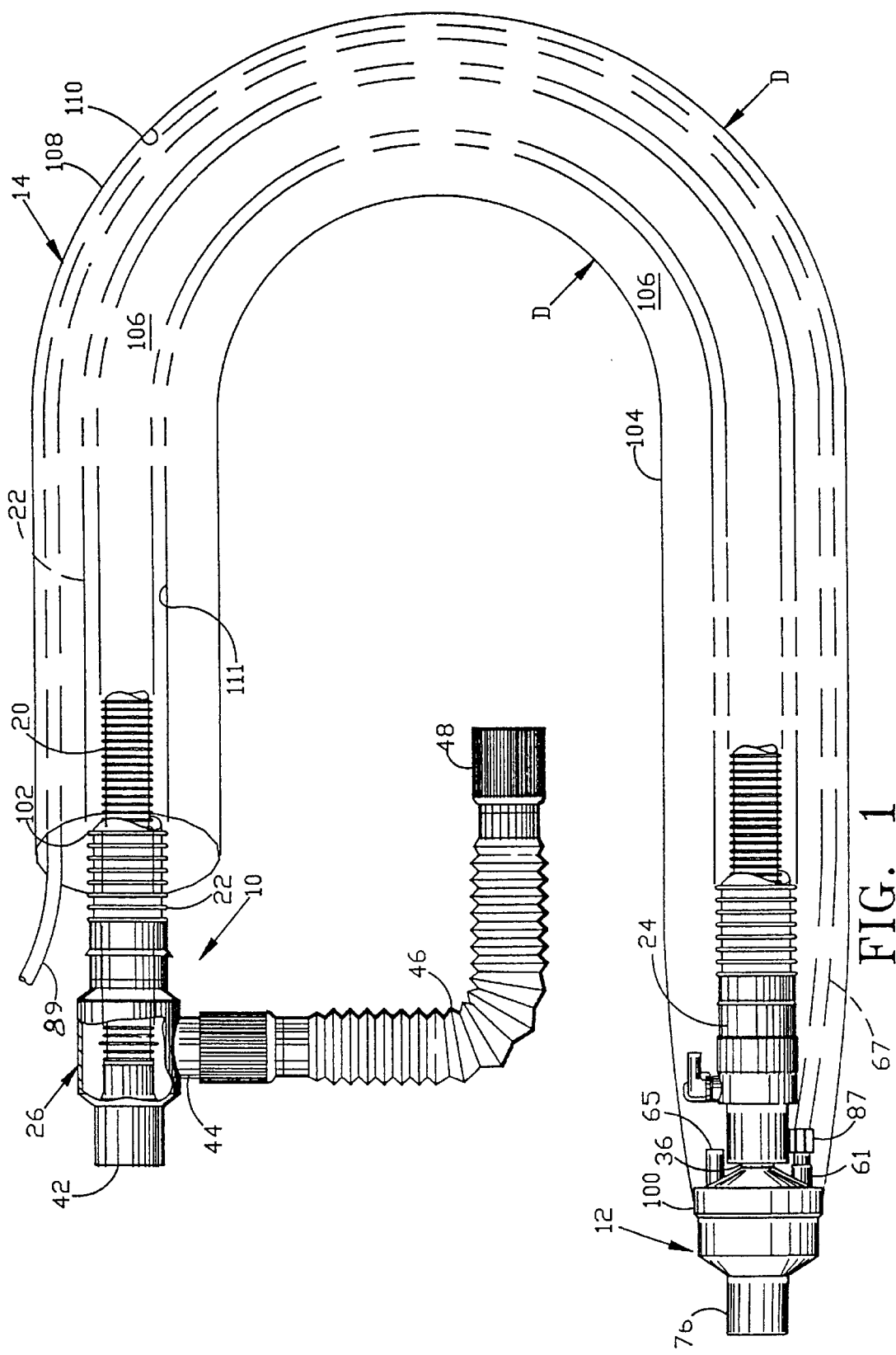
FIG. 1 is an elevational view of a unilimb type of breathing circuit to which is attached a sleeved filter of the present invention.
Figure 2:
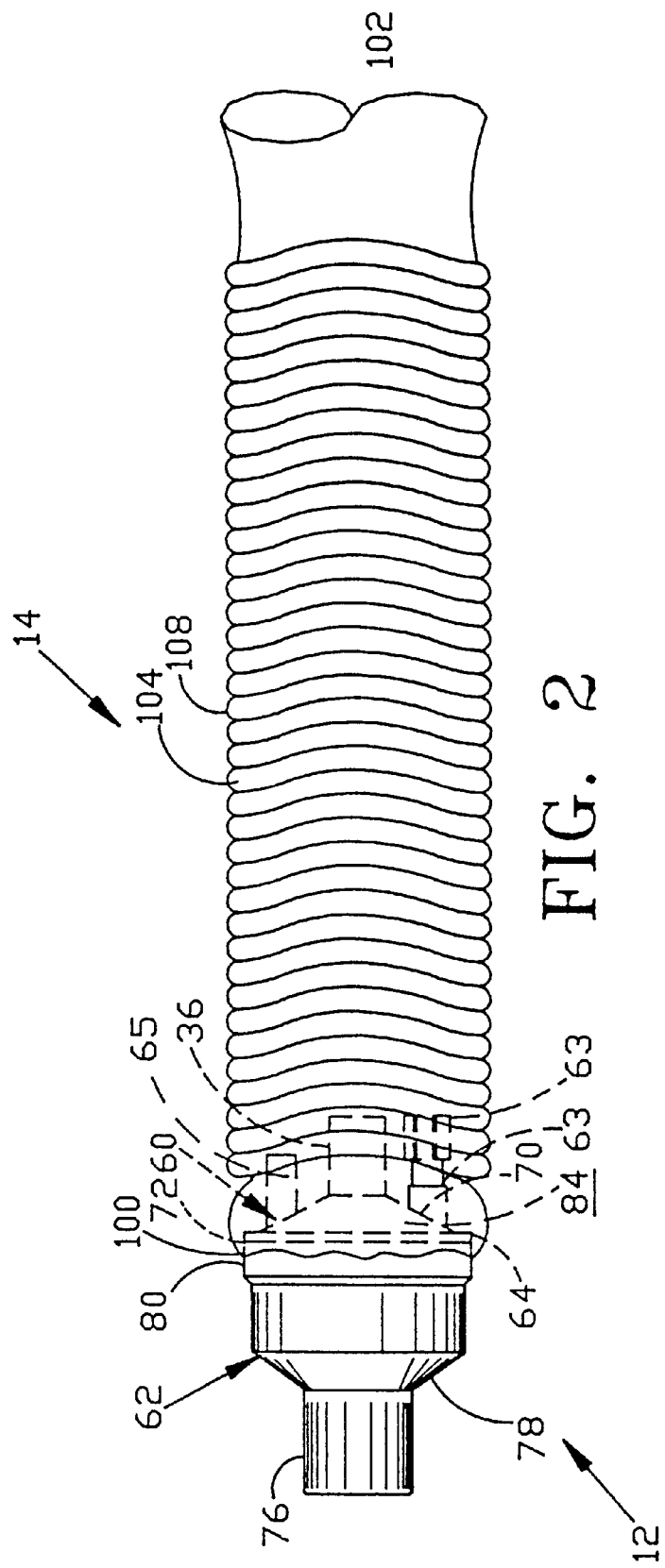
FIG. 2 is an elevational view of a filter and sleeve, wherein the sleeve is compressed for facilitating placement of the sleeve onto the breathing circuit.

FIGS. 1 and 2 show a breathing circuit 10 having a media container member, such as a filter member 12 and sleeve member 14 of the present invention attached thereto. The breathing circuit 10 shown in FIG. 1 is generally identical to the breathing circuit shown in Leagre and Burrow U.S. Pat. No. 5,404,873. The breathing circuit 10 includes an inspiratory tube 20 and an expiratory tube 22. As the breathing circuit 10 is a unilimb type breathing circuit, the expiratory tube 22 and inspiratory tube 20 are disposed coaxially with each other, with the inspiratory tube 20 being disposed within the interior of the expiratory tube 22.

Preferably, each of the inspiratory tube 20 and expiratory tube 22 include generally corrugated middle portions, which help to prevent the tubular portions of the expiratory tube 22 and inspiratory tube 20 from kinking when bent or twisted.

The breathing circuit 10 includes a patient end connector 24 and a machine end connector 26. The patient end connector 24 is provided for being coupled to the filter member 12. The machine end connector 26 is provided for connecting the breathing circuit 10 to an anesthesia machine (not shown), a ventilator (not shown), or to a carbon dioxide absorber (not shown) that is attached to an anesthesia machine. The machine end connector 26 includes an inspiratory port connector 42 which can be coupled to the inspiratory port of either the anesthesia machine or the carbon dioxide scrubber. The inspiratory port connector 42 is coupled directly to the inspiratory tube 20. The machine end connector 26 also includes an expiratory port connector 44 which can be coupled to a bendable gas tube 46. Bendable tube 46 includes a connector 48 for coupling the bendable tube 46 to the expiratory port of an anesthesia machine or a carbon dioxide absorber. The bendable tube 46 and expiratory port connector 44 are provided for conducting expiratory gas from the interior of the expiratory tube 22.

Figure 4:
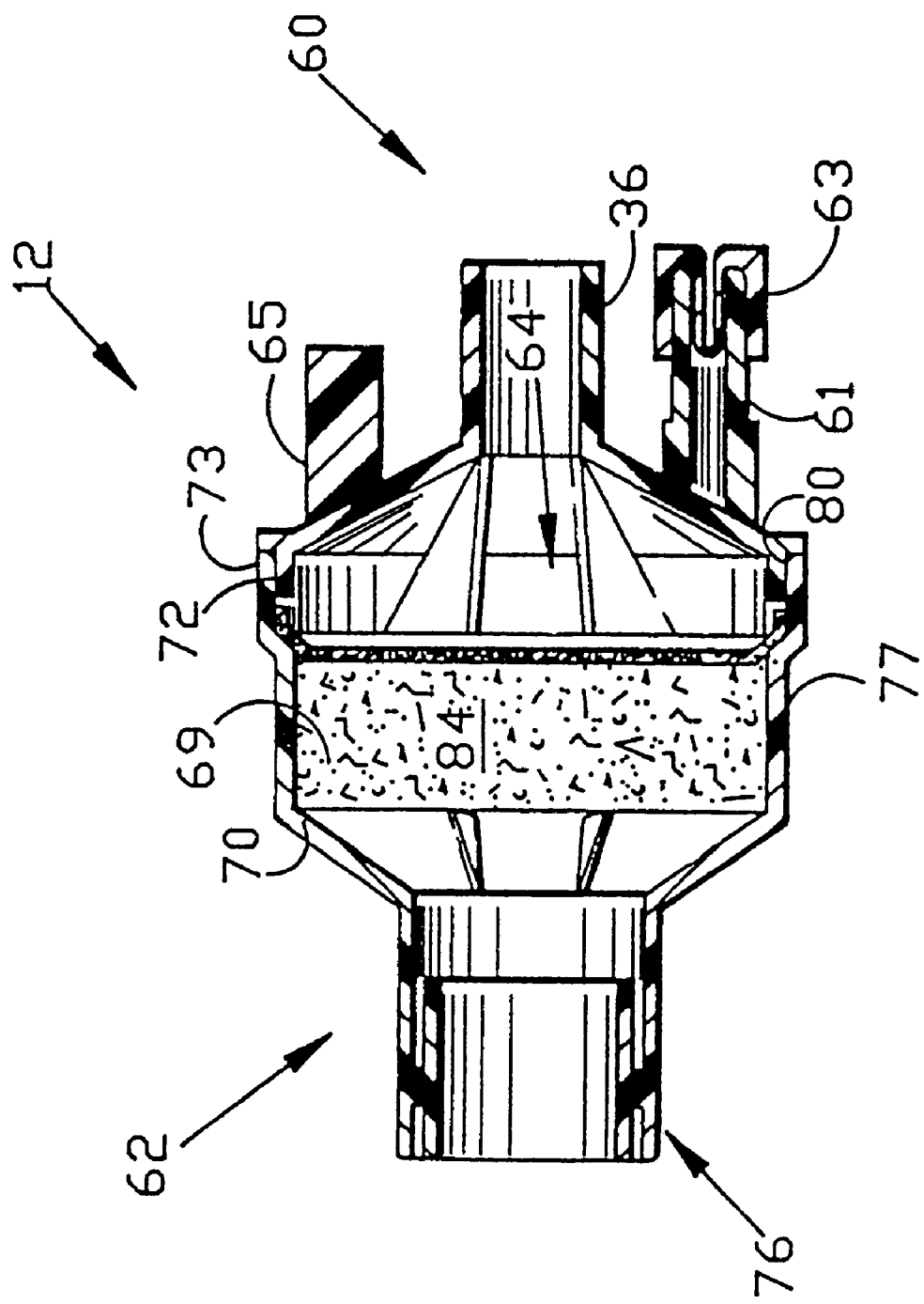
FIG. 4 is a sectional view of a filter useable with the present invention.

As best shown in FIGS. 2 and 4, the breathing filter member 12 is preferably made from a three piece construction that includes a generally part frusto-conically, part cylindrically-shaped first member 60, a generally part frusto-conically, part cylindrically-shaped second member 62, and a generally disk-shaped filter element 64 which is disposed in the interior of the breathing filter member 12. In certain filters, a heat and moisture exchange (HME) media 69 is also disposed within the interior of the filter member 12.

The first member 60 includes a first connector 36 which is sized and shaped for being received by the patient end connector 24 of the breathing circuit 10. The frusto-conical portion 70 of the first member 60 terminates in the cylindrical portion 73. The cylindrical portion 73 terminates in a female lip 72.

The first member 60 may also contain a luer-lock connector 61 having a removable cap 63. Connector 61 has a hollow interior for placing the interior of the filter 12 in gaseous communication with a gas sampling line 67 (FIG. 1) that can be attached to the filter (via the connector 61), for the purpose of monitoring the patient's expired gasses, and thus monitoring the patient's physical condition. A solid post 65 can also be provided for providing a holder for cap 63. When the gas line 67 is connected to the connector 61, the gas line is positioned adjacent to the exterior of the breathing circuit 20 along its length, but within the interior of the sleeve 14. The distal end of the gas line 67 includes a cap 87 having an opening through which the gas line 67 can pass. The cap 87 is provided for coupling the distal end of the gas line 67 to the connection 61, and hence to the interior of the filter 12. The gas line 67 should be at least as long as the length of the breathing circuit 20, so that the proximal end 89 of the gas line 67 may emerge from the interior of the sleeve adjacent the open end of the sleeve 14, which is adjacent to the machine end of the breathing circuit, to thus permit the proximal end 89 to be coupled to a gas sampling apparatus.

Second member 62 is generally similar in shape to first member 60, and includes a second connector 76; and a cylindrical portion 77; and a frusto-conical portion 78. The cylindrical portion 77 terminates in an male lip member 80 which is sized for being received snugly by female lip 72.

Second connector 76 is provided for connecting to a patient device, such as an anesthesia breathing mask (not shown), angle connector, an endotracheal tube (not shown) or other artificial airway device (not shown).

The first and second members 60, 62 of the filter member 12 are joined together so that the male and female lips 72, 80 engage snugly. In order to maintain the lips 72, 80 in engagement, the lips can be sonically welded, or bonded together. When the first and second members 60, 62 are so joined, they define a generally hollow interior 84. The disk-shaped filter element 64 and HME media 69 is disposed to extend radially in the interior 84 of the filter member 12, adjacent to the mated lips 72, 80. As shown in FIG. 4, the HME media 69 fills most of the interior 84 of the second member 62. The interior surface of the frusto-conical portion 70 of the second member includes a plurality of axially extending fins 85 for maintaining the HME media 84 in a spaced relation from the interior surface of the frusto-conical portion 70.

The filter element 64 and HME media 69 are sized to fit snugly against the lips 72, 80 so that any gases passing through the interior 84 of the filter member 12, between the first 36 and second 76 connectors, will pass through the filter element 64 and HME media 69. The filter element 64 is chosen to be of a type that is capable of trapping bacteria, viruses and other germs of interest thereon. Preferably, the filter member 12 should trap bacteria and viruses flowing in both directions. For example, bacteria and viruses that are resident in the patient should be trapped on the side of the filter element 64 adjacent to second connector 76, to thereby prevent the patient's bacteria and viruses from flowing into the inspiratory tube 20 and ultimately (in a rebreathing application) into the expiratory tube 22. Similarly, any bacteria or viruses that are resident in the interior of either the inspiratory tube 20 or expiratory tube 22 should be trapped on the surface of the filter element 64 adjacent to first connector 36, to prevent any such bacteria or viruses from finding their way into the patient (not shown).

Through this trapping of bacteria and viruses, it will be appreciated that the filter member 12, and in particular filter element 64 will prevent the transfer of many viruses and bacteria between the patient and the breathing circuit 10. By preventing the transfer of such viruses and bacteria, the breathing circuit 10 will help to reduce the transfer of bacteria and viruses between patients, if the breathing circuit 10 is used on multiple patients, so long as the filter member 12 is replaced for each new patient. An example of a filter that will function with the present invention is the Virobac II model filter that is manufactured by King Systems, the assignee of the instant application.

The HME media 69 is preferably chosen to be able to hold and retain moisture. An example of an HME media 69 that will function in the present invention is the Edith AME product manufactured by Datex-Engstrom of Bromma, Sweeden.

The sleeve member 14 has a first end 100 that is effectively closed through its attachment to the exterior surface of the filter member 12, adjacent to the lips 72, 80 of the filter member 12. The sleeve member 14 also includes a second, open end 102 that, when attached to a breathing circuit 10, is disposed adjacent to the machine end connector 26 of the breathing circuit 10. A middle portion 104 of the sleeve member 14 extends between the first end 100 and the second end 102. The tubular sleeve 14 includes an exterior wall surface 108, and an interior wall surface 110, which defines the sleeve 14.

Preferably, the sleeve member 14 is constructed of a clear, flexible material to enable the medical practitioner to view the expiratory and inspiratory tubes 20, 22 and easily manage the entire circuit 10. Additionally, the sleeve member 14 should be constructed of a light-weight, relatively inexpensive material, to help minimize the costs of producing the sleeve member 14. It has been found by applicant that a clear, extruded type polyethylene, polypropylene or polyvinyl film, having a thickness generally similar to a heavy duty plastic food storage bag will perform admirably in this role as a sleeve member 14.

The first end 100 of the sleeve member 14 is preferably attached to the exterior surface of the filter member 12, adjacent to the lips 72, 80. The diameter of the sleeve member 14 adjacent to the first end 100 should be sized to receive the filter member 12 snugly. Preferably, the first end 100 is joined to the filter element 12, by glue, tape, or bonding of some type. Alternately, the first end 100 can be sized for being received between the male and female lips 72, 80 of the filter element 12, so that the first end 100 becomes sandwiched between the lips 72, 80 to help maintain the position of the first end 100 of the sleeve member 14 on the filter element 12. After the lips 72, 80 and first end 100 are so sandwiched together, they can be bonded together, such as by sonic welding, glue or frictional engagement. Alternately, mechanical bonding techniques, such as adhesive tape, or mating protrusions and apertures formed in the respective male 80 and female 72 lips can be used to bond the lips 72, 80 and first end 100.

In any event, the goal is to ensure that the first end 100 is securely attached to the filter element 12, in a manner that will prevent the first end 100 from becoming dislodged from the filter element 12.

As alluded to above, the material from which the sleeve 14 is made should be a material which will provide a germ barrier, for preventing viruses and bacteria from passing through the exterior wall surface 108, into the interior of the sleeve 14, and likewise preventing bacteria and viruses from passing through the interior wall surface 110 to the exterior of the sleeve 14. The plastic materials discussed above will generally perform this function.

The purpose of the exterior wall surface 108 is to catch any viruses or bacteria that may fall thereon to prevent these viruses and bacteria from contacting the exterior wall 111 of the relatively exteriorly exposed expiratory tube 22. In this regard, it will be appreciated that a barrier need not be present to prevent bacteria or viruses from falling on the exterior surface of the inspiratory tube 20, as the expiratory tube 22 performs this function already.

The tubular sleeve 14 which is intended for use with a unilimb type circuit has a generally constant diameter D—D throughout its length, except perhaps that portion of its length adjacent to its first end 100, where it may be either slightly enlarged, or have a reduced diameter for snugly fitting onto the filter member 12. Preferably, the diameter D—D should be great enough to enable the sleeve 14 fit relatively loosely around the expiratory tube 22, to permit the sleeve 14 to be slid over the expiratory tube 22, but not so loosely that it gets in the way. As such, the diameter D—D of the sleeve 14 should be somewhere between 0.25" and about 2" greater than the diameter of the expiratory tube 22. Since the filter member 12 has a diameter greater than the diameter of the expiratory tube 22, a sleeve 14 having a diameter generally similar to the diameter of the widest part (adjacent lips 72, 80) of the filter member 12 will work well as the diameter D—D of the entire length of the sleeve member 14.

The sleeve member 14 also has a length which extends between its first end 100 and its second end 102. The length should be chosen to cover most (if not all) of the length of the breathing circuit 10, up to the expiratory port connector 44, over which the sleeve member 14 can generally not pass. Due to the relatively thin, flexible nature of the sleeve member 14, its length can be greater than the length of the breathing circuit 10, with the excess being "bunched up" adjacent to the expiratory connector 44. Preferably, the sleeve 14 has a length of between about 40 inches and 120 inches, which corresponds to a length equal to or slightly greater than the standard relaxed lengths of unilimb breathing circuits.

Turning now to FIG. 2, it will be noticed that the sleeve member 14 is generally somewhat bunched up. This is the position that the sleeve member 14 would preferably be in prior to its attachment to the breathing circuit 10. To place the filter member 12 and sleeve member 14 onto a breathing circuit 10, the sleeve member 14 is bunched up as shown in FIG. 2. The open end 102 is slid over the patient end connector 24 of the breathing circuit 10. Returning now to FIG. 1, filter member 12 is then pushed toward the patient end connector 24, as the sleeve member 14 is pulled over the breathing circuit 10, to a point wherein the first connector 36 of the filter member 12 can be coupled to the patient end connector 24 of the breathing circuit 10. The second end 102 is then pulled along the breathing circuit 10, until the sleeve member 14 is either stretched to its full length, or else the second end 102 contacts the expiratory connector 44.

To remove the device, one can grab the filter member 12, in a position adjacent to the first end 100 of the sleeve, and pull the filter member 12 away from the patient end connector 24, to separate the first connector 36 of the filter member 12 from the patient end connector 24. When disconnection is achieved, the filter member 12 can then be pulled in a direction away from the patient end connector 24. As the filter member 12 is coupled to the first end 100 of the sleeve member 14, the pulling of the filter member 12 away from the patient end connector 24, will pull off the middle portion 104 and second end 102 of the sleeve member 14 from the breathing circuit 10, to effect the removal of the filter member 12/sleeve member 14 combination from the breathing circuit 10.

During use, the exterior wall surface 108 of the sleeve member 14 is positioned over the exterior surface of the expiratory tube 22 in a manner that permits it to stop any virus and bacteria containing bodily fluids (or other virus or bacteria containing materials) from reaching the exterior surface 108, thereby preventing any such fluids or other materials from contacting the exterior surface of the expiratory tube 22, thus helping to maintain the exterior surface of the expiratory tube 22, and hence the breathing circuit 10, in a relatively germ-free state. Additionally, if viruses and bacteria are already resident on the exterior surface of the expiratory tube, the placement of the sleeve member 14 over the expiratory tube 22 helps to prevent any such viruses or bacteria from being transferred throughout the operating theater (or patient room), to thereby help to prevent any such viruses or bacteria that are resident on the exterior of the expiratory tube 22 from coming into contact with the patient or medical personnel, and not impacting their health.

Figure 3:
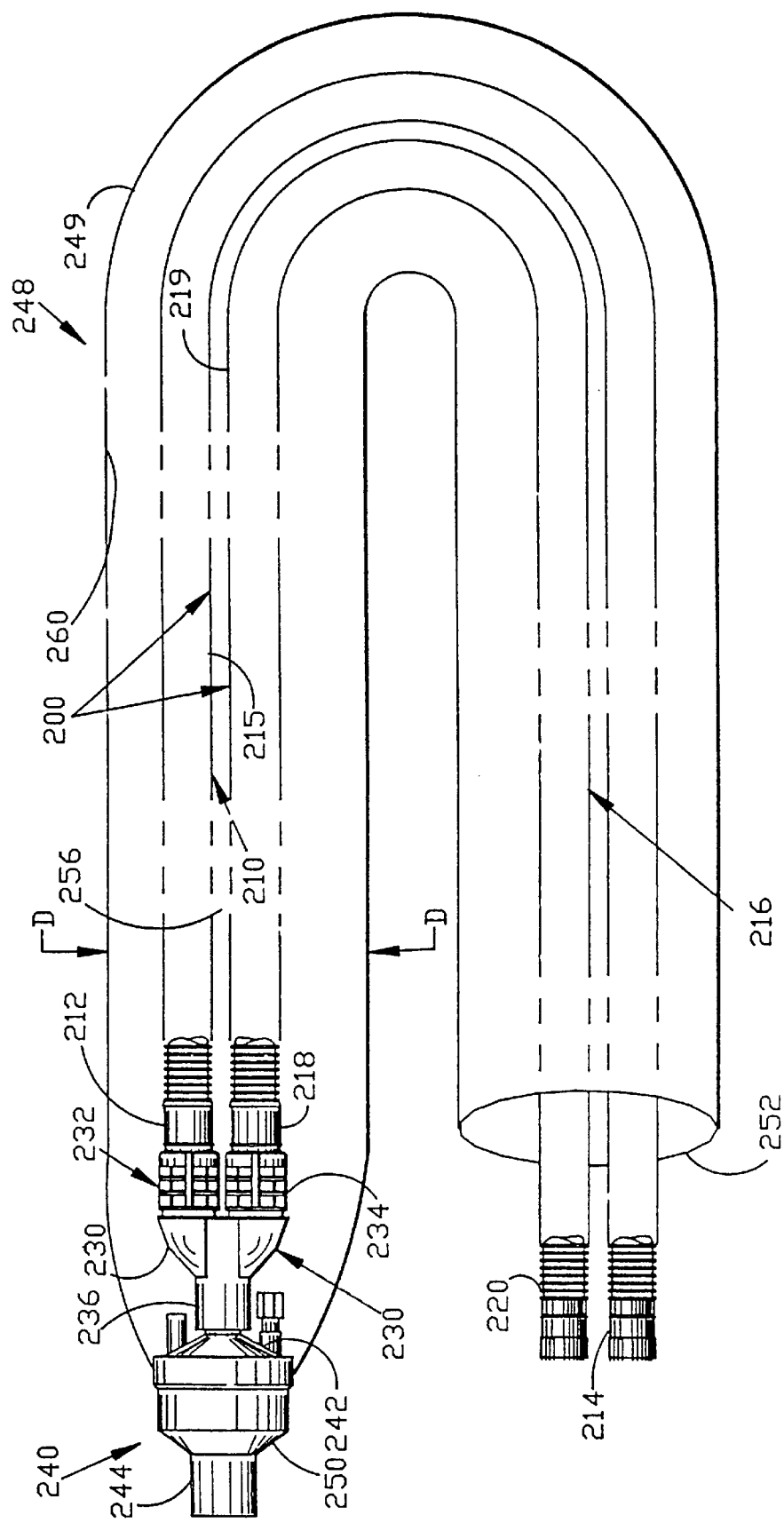
FIG. 3 is an alternate embodiment sleeved filter of the present invention especially adaptable for use with dual-limb breathing circuits.

An alternate embodiment filter member 240 and sleeve member 248 device is shown in FIG. 3. In FIG. 3, the filter member 240 is generally similar to filter member 12 shown in FIGS. 1 and 2, but the sleeve member 248 is configured somewhat differently, to accommodate a dual-limb breathing circuit 200. Dual-limb breathing circuit 200 contains an inspiratory tube 210 having a patient end connector 212, and a machine end connector 214. The inspiratory tube 210 includes a singe-lumen tube portion 215 which is disposed between the patient end connector 212 and the machine end connector 214. The dual-limb breathing circuit 200 also includes an expiratory tube 216 having a patient end connector 218, and a machine end connector 220, with a single-lumen tube portion 219 extending between the patient end connector 218 and machine end connector 220.

Dual-limb breathing circuits of the type described above are well known in prior art, and pre-date the unilimb breathing circuits of the type described in FIGS. 1 and 2. A 'Y' component 230 is provided for connecting the patient end connectors 212, 218 of the inspiratory tube 210 and expiratory tube 216 to the filter 240. The 'Y' tube 230 includes a first connector 232 for mating onto the patient end 212 of the inspiratory tube 210, and a second connector 234 for mating onto the patient end 218 of the expiratory tube 216. The 'Y' tube also includes a third connector 236 for mating onto the first connector 242 of the filter member 240.

As discussed above, the filter member 240 of the embodiment shown in FIG. 3 may be identical to the filter member 12 of the embodiments shown in FIGS. 1 and 2. The filter member 240 also includes a second connector 244, and a filter element, and possibly HME media (e.g., HME media 69 in FIG. 4), that is disposed in the interior of the filter member 240.

The sleeve member 248 includes a relatively, reduced diameter first end 250 which is preferably sealingly engaged to the filter member 240 in a manner similar to the manner in which the first end 100 of sleeve 14 is sealingly engaged to the filter member 12 of the embodiment shown in FIGS. 1 and 2. The sleeve member 248 also includes a second, open end 252, and a middle portion 249 which extends between the first end 250 and the second end 252. The sleeve member 248 can be made from material generally identical to the material discussed above in connection with sleeve member 14 of the embodiment shown in FIGS. 1 and 2. The sleeve member 248 has an exterior wall surface 249 and an interior wall surface 260 which define a generally hollow interior 256 for receiving the inspiratory and expiratory tubes 210, 216 respectively.

Because the inspiratory and expiratory tubes 210, 216 of the dual-limb circuit are not collinear, as they are in the unilimb circuit 10 of FIG. 1, the diameter D—D of the sleeve must be greater to accommodate the relatively greater bulk of the dual-limb breathing circuit 200. The sleeve member 248 also has a length L which is defined as that length between the first end 250 of the sleeve 248, and the second end 252 of the sleeve member 248.

In the embodiment shown in FIG. 3, the sleeve member 248 has a generally constant diameter throughout the majority of its length, except for that portion adjacent to the first end 250 of the sleeve member 248, which has a relatively reduced diameter. Alternately, the sleeve member 248 can be designed to have a diameter which increases as one moves from the first end 250 to the second end 252, thus giving the sleeve member 248 a somewhat "A" shaped or frusto-conical configuration. For example, the first end 250 of the sleeve member 248 can have a diameter of between about 2 inches and 3 inches, which expands outwardly along the length of the sleeve member 248, so that the second end 252 of the sleeve member 248 has a diameter of between about 5 inches and 8 inches. Preferably the sleeve member 248 has a length of between about 40 inches and 120 inches, which corresponds to a length similar, or slightly longer than the standard relaxed lengths of expiratory and inspiratory tubes 210, 216.

However, it will also be appreciated that one function that can be served by the sleeve member 248 is to keep the inspiratory tube 210 and expiratory tube 216 in close proximity throughout the majority of their length. By keeping the inspiratory tube 210 and expiratory tube 216 in close proximity, the sleeve member 248 can help reduce clutter in the operating theater, of the type that normally occurs when one uses a dual-limb circuit.

From a virus and bacteria barrier standpoint, sleeve member 248 performs its function in a manner generally similar to the manner in which sleeve member 14 of FIGS. 1 and 2 performs its function. Further, sleeve member 248 and filter member 240 may be attached to, and detached from the dual-limb breathing circuit 200, in a manner generally similar to that discussed above in connection with the embodiments of FIGS. 1 and 2.

Having described the invention in detail, it will be appreciated that some modifications exist within the scope and spirit of the invention.

What is claimed is:

1. A sleeved breathing filter apparatus for preventing contamination of both the interior and exterior of a breathing device, the sleeved filter breathing apparatus comprising:

a filter container member having a hollow interior, a first connector, a second connector and a filter element disposed within the hollow interior such that gases passing between the first connector and the second connector must pass through the filter element, the first connector capable of being connected to and disconnected from the breathing device by the user at the site of use; and a tubular sleeve member having a first end and a second end, the first end being sealingly engaged to the filter container member, the tubular sleeve member and the second end thereof capable of being expanded by the user at the site of use to loosely surround a portion of the breathing device;

whereby, when a contamination source is operably connected to the second connector and the breathing device is operably connected to the first connector, contaminants passing through the second connector are substantially prevented from contacting the interior of the breathing device by the filter element and contaminants passing around the second connector are substantially prevented from contacting the exterior of the breathing device by the sleeve member.

2. The sleeved breathing filter apparatus of claim 1, wherein the filter container member includes a first enclosure half having an external end and an internal end, the external end including the first connector of the filter container member;

a second enclosure half having an external end and an internal end, the external end including the second connector of the filter container member;

the internal end of the first enclosure half being sealingly connected to the internal end of the second enclosure half.

3. The sleeved breathing filter apparatus of claim 2 wherein the internal end of the first enclosure half has a female lip having a larger diameter than the external end of the first enclosure half, the internal end of the second enclosure half has a male lip having a larger diameter than the external end of the second enclosure half, the internal end of the first enclosure half being sealingly connected to the internal end of the second enclosure half by mating the female lip of the first enclosure half with the male lip of the second enclosure half, the filter element extending radially in the interior of the filter container member, and the filter element being sized to fit snugly in the interior of the filter container member and disposed adjacent to the area where the first enclosure half is sealingly connected to the second enclosure half.

4. The sleeved breathing filter apparatus of claim 3 wherein the first end of the sleeve member is sealingly engaged to the filter container member by sandwiching the first end of the sleeve member between the female lip of the first enclosure half of the filter container member and the male lip of the second enclosure half of the filter container member.

5. The sleeved breathing filter apparatus of claim 1, wherein the sleeve member has a generally constant sleeve diameter.

6. The sleeved breathing filter apparatus of claim 5, wherein the filter container member includes
   a first enclosure half having an external end and an internal end, the external end including the first connector of the filter container member;
   a second enclosure half having an external end and an internal end, the external end including the second connector of the filter container member;
   the internal end of the first enclosure half being sealingly connected to the internal end of the second enclosure half.

7. The sleeved breathing filter apparatus of claim 6, wherein the internal end of the first enclosure half has a female lip, and the internal end of the second enclosure half has a male lip, the internal end of the first enclosure half being sealingly connected to the internal end of the second enclosure half by mating the female lip of the first enclosure half with the male lip of the second enclosure half, and the first end of the sleeve member being sealingly engaged to the filter container member by sandwiching the first end of the sleeve member between the female lip of the first enclosure half and the male lip of the second enclosure half.

8. The sleeved breathing filter apparatus of claim 1, wherein the sleeve member has a sufficient length between the first end and the second end so that the sleeve member can extend along substantially the entire length of the breathing device.

9. The sleeved breathing filter apparatus of claim 1, wherein the sleeve member has a first section adjacent to the first end and a second section adjacent to the second end; the first section having an increasing diameter which increases as the first section gets further from the first end, the second section and second end having a generally constant diameter equal to the maximum diameter of the first section, whereby, when a multi-limb breathing device is connected to the second connector, the generally tubular sleeve and second end of the sleeve member loosely surround the multi-limb breathing device.

10. The sleeved breathing filter apparatus of claim 9, wherein the filter container member includes
    a first enclosure half having an external end and an internal end, the external end including the first connector of the filter container member;
    a second enclosure half having an external end and an internal end, the external end including the second connector of the filter container member;
    the internal end of the first enclosure half being sealingly connected to the internal end of the second enclosure half.

11. The sleeved breathing filter apparatus of claim 10, wherein the internal end of the first enclosure half has a female lip, and the internal end of the second enclosure half has a male lip, the internal end of the first enclosure half being sealingly connected to the internal end of the second enclosure half by mating the female lip of the first enclosure half with the male lip of the second enclosure half, and the first end of the sleeve member being sealingly engaged to the filter container member by sandwiching the first end of the sleeve member between the female lip of the first enclosure half and the male lip of the second enclosure half.

12. The sleeved breathing filter apparatus of claim 1, wherein the first end of the sleeve member has a first diameter, and the second end of the sleeve member has a second diameter, the second diameter being greater than the first diameter.

* * * * *